(12) United States Patent
Jain et al.

(10) Patent No.: US 11,738,028 B2
(45) Date of Patent: Aug. 29, 2023

(54) THERAPEUTIC REGIMEN

(71) Applicant: Novartis AG, Basel (CH)

(72) Inventors: Jay Prakash Jain, Pleasanton, CA (US); Franz Joel Leong, Singapore (SG); Cornelis Winnips, Flueh (CH); Marie-Christine Wolf, St. Louis (FR)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 17/388,277

(22) Filed: Jul. 29, 2021

(65) Prior Publication Data

US 2022/0088022 A1    Mar. 24, 2022

Related U.S. Application Data

(63) Continuation of application No. 16/669,275, filed on Oct. 30, 2019, now abandoned, which is a continuation of application No. 15/961,394, filed on Apr. 24, 2018, now abandoned.

(30) Foreign Application Priority Data

Apr. 24, 2017  (IN) .............................. 201711014459

(51) Int. Cl.
| | |
|---|---|
| *A61K 31/522* | (2006.01) |
| *A61K 31/137* | (2006.01) |
| *A61P 33/06* | (2006.01) |
| *A61K 31/4985* | (2006.01) |
| *A61K 45/06* | (2006.01) |

(52) U.S. Cl.
CPC .......... *A61K 31/522* (2013.01); *A61K 31/137* (2013.01); *A61K 31/4985* (2013.01); *A61K 45/06* (2013.01); *A61P 33/06* (2018.01); *A61K 2300/00* (2013.01)

(58) Field of Classification Search
CPC ................ A61K 31/522; A61K 31/137; A61K 31/4985; A61K 45/06; A61P 33/06
See application file for complete search history.

(56) References Cited

U.S. PATENT DOCUMENTS

| | | |
|---|---|---|
| 4,870,073 A | 9/1989 | Watjen et al. |
| 2004/0186148 A1 | 9/2004 | Shankar et al. |
| 2008/0242862 A1 | 10/2008 | Calderwood et al. |

FOREIGN PATENT DOCUMENTS

| | | |
|---|---|---|
| CN | 1042535 A | 5/1990 |
| CN | 101357922 A | 2/2009 |
| CN | 103006564 A | 4/2013 |
| EP | 362810 B1 | 5/1993 |
| EP | 1382607 B1 | 8/2009 |
| FR | 2856688 A1 | 12/2004 |
| WO | 9202217 A1 | 2/1992 |
| WO | 9315727 A1 | 8/1993 |
| WO | 9730053 A1 | 8/1997 |

(Continued)

OTHER PUBLICATIONS

Ayoub. et al., "Inhibition of Heterotrimeric G Protein Signaling by a Small Molecule Acting on G alpha Subunit," J. Biol. Chem. 284(42):29136-29145, Oct. 16, 2009.

(Continued)

*Primary Examiner* — San Ming R Hui
(74) *Attorney, Agent, or Firm* — McCarter & English, LLP; Xin Zhang

(57) ABSTRACT

The present invention relates to dosing regimen of a new antimalarial drug, as monotherapy or combination therapy.

21 Claims, 3 Drawing Sheets

Mean plasma concentration-time profiles of lumefantrine following oral administration of single 480 mg dose as conventional tablet or SDF variant-1 and SDF variant-2 under fasting conditions (humans)

Cohort 1: 480 mg conventional tablets (Fasting); Cohort 2: 480 mg SDF variant-1 capsules (Fasting); Cohort 3: 480 mg SDF variant-2 capsules (Fasting)

(56) References Cited

FOREIGN PATENT DOCUMENTS

| | | | |
|---|---|---|---|
| WO | 9964401 | A2 | 12/1999 |
| WO | 0002881 | A2 | 1/2000 |
| WO | 0039130 | A2 | 7/2000 |
| WO | 0134203 | A1 | 5/2001 |
| WO | 0149322 | A1 | 7/2001 |
| WO | 0210140 | A2 | 2/2002 |
| WO | 02053558 | A1 | 7/2002 |
| WO | 02096348 | A2 | 12/2002 |
| WO | 03004498 | A1 | 1/2003 |
| WO | 03082817 | A2 | 10/2003 |
| WO | 04028541 | A2 | 4/2004 |
| WO | 04058266 | A1 | 7/2004 |
| WO | 04058762 | A1 | 7/2004 |
| WO | 04103276 | A2 | 12/2004 |
| WO | 07017423 | A2 | 2/2007 |
| WO | 07117180 | A1 | 10/2007 |
| WO | 07124423 | A2 | 11/2007 |
| WO | 08006085 | A2 | 1/2008 |
| WO | 08094737 | A2 | 8/2008 |
| WO | 09005675 | A1 | 1/2009 |
| WO | 09095253 | A1 | 8/2009 |
| WO | 09095254 | A1 | 8/2009 |
| WO | 09155388 | A1 | 12/2009 |
| WO | 11006143 | A2 | 1/2011 |

OTHER PUBLICATIONS

Bienaymé H, et al., "A New Heterocyclic Multicomponent Reaction For the Combinatorial Synthesis of Fused 3-Aminoimidazoles," Angew Chem Int Ed Engl. Sep. 4, 1998;37(16):2234-2237.

Rongxian, et al., Chemical Abstracts, vol. 97(1) p. 575 Abstract No. 5938z XP002119016, "Studies on antimalarial agents", p. 575, col. 1 (1982) (English abstract only).

Doerig et al., "Stopping malaria parasites dead in their tracks", Nature Chemical Biology 4(6):334-335, Jun. 2008.

Groebke, et al, "Synthesis of Imidazo[1,2-a] annulated Pyridines, Pyrazines and Pyrimidines by a Novel Three-Component Condensation" Synlett, pp. 661-663, 1998.

Kercher, et al, "Diversification of the Three-Component Coupling of 2-Aminoheterocycles, Aldehydes, and Isonitriles: Efficient Parallel Synthesis of a Diverse and Druglike Library of Imidazo- and Tetrahydroimidazo[1,2-alpha] Heterocycles" J. Comb. Chem, 9:1177-1187, 2007.

Kuhen, et al., "KAF156 is an antimalarial clinical candidate with potential for use in prophylaxis, treatment, and prevention of disease transmission" Antimicrobial Agents and Chemotherapy, 58(9):5060-5067, 2014.

Leong, et al., "A First-in-Human Randomized, Double-Blind, Placebo-Controlled, Single-and Multiple-Ascending Oral Dose Study of Novel Imidazolopiperazine KAF156 to Assess Its Safety, Tolerability, and Pharmacokinetics in Healthy Adult Volunteers" Antimicrob Agents Chemother. 58(11): 6437-6443, Nov. 2014.

Lewandowicz, et al., "Energetic Mapping of Transition State Analogue Interactins with Human and Plasmodium falciparum Purine Nucleoside Phosphorylases", The Journal of Biological Chemistry 280(34):30320-30328, Aug. 26, 2005.

Lyon, et al., "Glyoxylic Acid and MP-Glyoxylate; Efficient Formaldehyde Equivalents in the 3-CC of 2-Aminoazines, Aldehydes, and Isonitriles" Organic Letters 6(26):4989-4992, 2004.

Menard, et al., "A worldwide Map of Plasmodium Falciparum K13-Propeller Polymorphisms" N. Engl. J. Med. 374(25):2453-64, 2016.

Scarpelli, et al., "Studies of the metabolic stability in cells of 5-(trifluoroacetyl)thiophene-2-carboxamides and dentification of more stable class I histone deacetylase (HDCC) inhibitors", Bioorganic and Medicinal Chemistry Letters 18:6078-6082, 2008.

Tun, et al., "Spread of artemisinin-resistant Plasmodium falciparum in Myanmar: a cross-sectional survey of the K13 molecular marker" Lancet Infect Dis. 15(4):415-21, 2015.

Varma, et al., "Microwave-accelerated three-component condensation reaction on clay: solvent-free synthesis of imidazo[1,2-a] annulated pyridines, pyrazines and pyrimidines", Tetrahedron Letters 40:7665-7669, 1999.

White, et al., "Antimalarial Activity of KAF156 in Falciparum and Vivax Malaria" New England Journal of Medicine, 375(12):1152-1160, 2016.

World Health Organization Technical Report Series 805, Report of WHO Scientific Group, "Practical chemotherapy of malaria", pp. 124-126, 1990).

CAS RN 956018-35-2 (entered into STN Nov. 27, 2007).

CAS RN 956018-99-8 (entered into STN Nov. 27, 2007).

CA 113(5):34389a, Sethi, et al, "Systemic toxicity study of a new schizontocidal antimalarial drug, Arteether, in rats and monkeys Indian" Journal Of Parasitology 12(2):223-235, I 988.

CA 103:134524, Lin et al., 1985 (English abstract).

Wang et al., Chemical Abstracts vol. 101, p. 385 Abstract No. 136941u "Studies on the Stability of Fluorenemethanol Antimalarial in Linoleic and Soft Capsules" 1984.

Combrinck, et al., "Insights into the Role of Heme in the Mechanism of Action of Antimalarials" ACS Chem. Biol. 8(1):133-137, 2013.

Rongxian, et al., "Recent Progress in Research on antimalarials in China," Chinese Journal of Pharmaceuticals, vol. 20(8):372-376, 1989 (english abstract).

Deng, Rong-Xian et al., Chemical Abstracts, vol. 114(1) p. 595 Abstract No. 6046p (1991).

Chemical Abstracts 97:28538h, Wang Yunling et al., "Enhancement of bioavailability of a hydrophobic fluorenemethanol antimalarial by oleic acid in soft gelatin capsules", Yaoxue Tongbao, vol. 17, No. 1, 4-7, (1982).

Deng, Chemical Abstracts 112(7):1 Abstract No. 48094s, Feb. 12, 1990.

Wang Yunling et al., "Stability of antimalarial fluorenemethanol in soft capsules", Yaowu Fenxi Zazhi, vol. 4, No. 2, pp. 84-87 (1984).

Figure 1: Mean plasma concentration-time profiles of lumefantrine following oral administration of single 480 mg dose as conventional tablet or SDF variant-1 and SDF variant-2 under fasting conditions (humans)
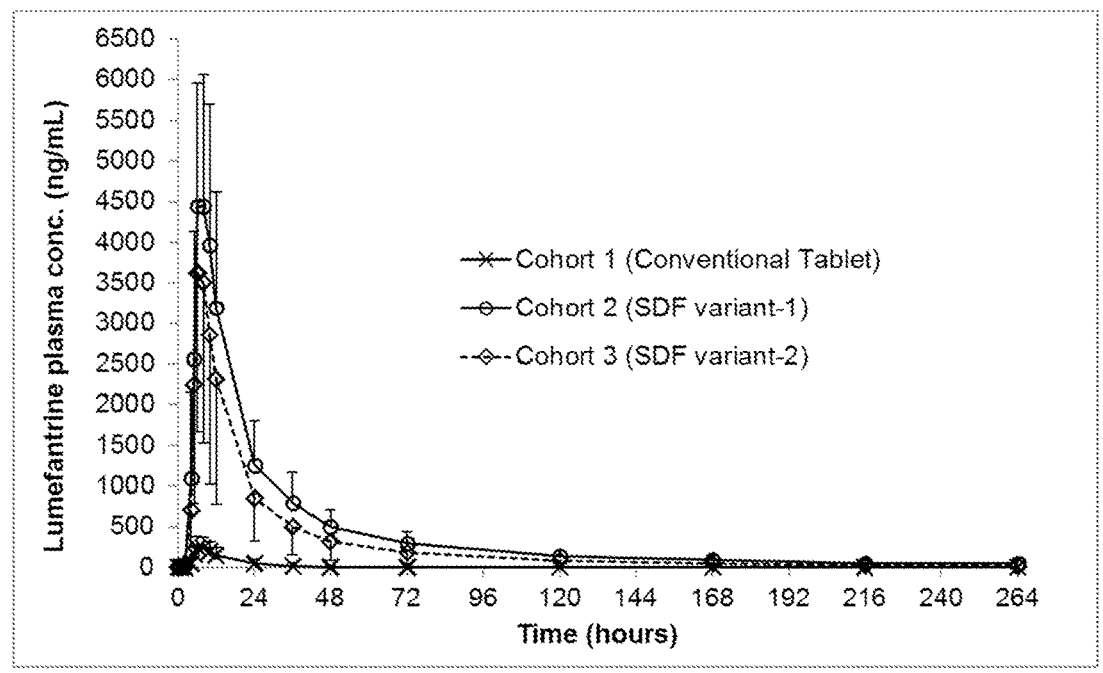
Cohort 1: 480 mg conventional tablets (Fasting); Cohort 2: 480 mg SDF variant-1 capsules (Fasting); Cohort 3: 480 mg SDF variant-2 capsules (Fasting)

THERAPEUTIC REGIMEN

CROSS-REFERENCE TO RELATED APPLICATIONS

This application is a continuation of U.S. application Ser. No. 16/669,275, filed Oct. 30, 2019 which claims the benefit of priority to U.S. application Ser. No. 15/961,394, filed Apr. 24, 2018, and Indian Patent Application No. 201711014459, filed Apr. 24, 2017, the contents of which is incorporated herein by reference.

FIELD OF THE INVENTION

The invention provides an imidazolepiperazine, such as 2-amino-1-(2-(4-fluorophenyl)-3-(4-fluorophenylamino)-8,8-dimethyl-5,6-dihydroimidazo[1,2-a]pyrazin-7(8H)-yl)ethanone (KAF156), or a pharmaceutically acceptable salt thereof, for use in the prevention or treatment of malaria, optionally in combination with another anti-malaria drug. The invention relates to methods of preventing, treating, delaying the symptoms or ameliorating the conditions associated with malaria, comprising administering to a subject in need thereof said imidazolepiperazine or a pharmaceutically acceptable salt thereof, optionally in combination with another anti-malaria drug. Specifically, the invention provides new dosing regimen of 2-amino-1-(2-(4-fluorophenyl)-3-(4-fluorophenylamino)-8,8-dimethyl-5,6-dihydroimidazo[1,2-a]pyrazin-7(8H)-yl)ethanone, or a pharmaceutically acceptable salt thereof, and combinations comprising said compound, and another anti-malaria drug.

BACKGROUND OF THE INVENTION

Malaria is one of the most important infectious diseases, which threatens about 3.2 billion people, almost half of the world's population. Despite increasing international efforts for malaria control, in 2015, there were 214 million cases worldwide of malaria and 438 000 deaths according to the latest estimates of the World Health Organization. Sub-Saharan Africa carries a disproportionately high share of the global malaria burden. In 2015, the region was home to 88% of malaria cases and 90% of malaria deaths. Also, in areas with high transmission of malaria, children under 5 are particularly susceptible to infection, illness and death; more than two thirds (70%) of all malaria deaths occur in this age group (306 000 estimates deaths in 2015).

Malaria is an infectious disease caused by four protozoan parasites: *Plasmodium falciparum*; *Plasmodium vivax*; *Plasmodium ovale*; and *Plasmodium* malaria. These four parasites are typically transmitted by the bite of an infected female *Anopheles* mosquito. Malaria is a problem in many parts of the world and over the last few decades the malaria burden has steadily increased. An estimated 1-3 million people die every year from malaria—mostly children under the age of 5. This increase in malaria mortality is due in part to the fact that *Plasmodium falciparum*, the deadliest malaria parasite, has acquired resistance against nearly all available antimalarial drugs, with the exception of the artemisinin derivatives.

Malaria is characterized by fever, headache, muscle ache, back pain, joint pains, nausea, sometimes vomiting and coughs; in severe case it leads to coma and finally it causes death.

Standard antimalarial drugs such as chloroquine (CQ), pyrimethamine (PYR), sulfadoxine (SFDX) and mefloquine (MEF) have become largely ineffective in many malaria endemic regions. The only exceptions are the artemisinin-based combination therapies (ACTs) such as Novartis' Coartem®/Riamet® and Eurartesim®, current standard-of-care for *P. falciparum* malaria.

Coartem® is a fixed combination of artemether, an artemisinin derivative, and lumefantrine. Dosing is weight-based and the standard dose is composed of 80 mg artemether and 480 mg lumefantrine twice daily for three days. As stated in the prescribing information Coartem must be administered with high fat food, since food is known to increase the bioavailability of lumefantrine by up to 16-fold and of artemether by up to 3-fold. The administration of Coartem with food is also important to achieve sufficient exposure of lumefantrine up to day 7, which is required for high cure rate. In acute malaria illness and in malaria endemic countries, non-adherence to this treatment requirement could lead to treatment failure.

Some recent reports (Menard et al 2016; A worldwide map of *Plasmodium falciparum* K13-Propeller polymorphisms; N. Engl. J. Med; 374(25):2453-64) suggest that decades of continuous use of artemisinin and bisquinoline derivatives as monotherapies may have fostered the emergence of drug resistance in *Plasmodium* species in Southeast Asia. Reduced in vitro susceptibility of *P. falciparum* to artemisinin in this region has been documented. Recent studies showed that artemisinin resistance extends over more of southeast Asia than had previously been known, and is now present close to the border with India (Menard et al 2016). If widespread artemisinin drug resistance was to occur, malaria pharmacotherapy would be severely impaired. This finding signifies that spread of resistance is inevitable, thus there is urgent need for new antimalarials with new mechanism of actions (Tun et al 2015; Spread of artemisinin-resistant *Plasmodium falciparum* in Myanmar: a cross-sectional survey of the K13 molecular marker; Lancet Infect Dis; 15(4):415-21). In addition, current *falciparum* malaria treatments require at least a 3-day dosing regimen which may contribute to therapeutic non-compliance in some patients. Indeed, patients often have resolution of clinical symptoms within 1 to 2 days and may neglect taking final doses. This may contribute to the development of drug resistance.

2-amino-1-(2-(4-fluorophenyl)-3-(4-fluorophenylamino)-8,8-dimethyl-5,6-dihydroimidazo[1,2-a]pyrazin-7(8H)-yl)ethanone (KAF156) is the first drug from a different and novel class of drugs called imidazolepiperazines. This compound is structurally distinct from currently marketed antimalarial drugs and other experimental antimalarial compound classes currently in development. The mechanism of action of KAF156 is still being characterized, but may be related to a previously uncharacterized gene (*Plasmodium falciparum* cyclic amine resistance locus, Pfcarl). KAF156 kills/inhibits the erythrocytic replication life cycle stages (blood stages) of the two main causative agents of human malaria, *P. falciparum* and *P. vivax*, both at low nanomolar EC50s (in vitro). In addition, KAF156 has shown activity in liver stage models of *Plasmodium* infection, conferring causal prophylactic protection in animal infection models. Limited evidence of gametocyticidal activity may confer transmission blocking activity. KAF156 has not demonstrated activity against liver hypnozoites and therefore has a low probability to be used for a radical cure for *P. vivax*. Also, KAF156 is equally potent against drug-sensitive and a broad panel of drug resistant malaria strains (Kuhen et al 2014 "KAF156 is an antimalarial clinical candidate with potential for use in prophylaxis, treatment, and prevention of disease transmission; Antimicrobial Agents and Chemotherapy; 2014; 58(9):5060-5067).

By killing the malaria parasite at its early, asymptomatic liver stage, KAF156 has a potential to serve as a prophylactic treatment, preventing the disease to spread into the blood stream, and thus to pass into a mosquito which could otherwise infect another human.

KAF156 was previously tested in malaria in uncomplicated adult malaria patients, either in a 3 day dosing with a dose of 400 mg/day (patients affected by with *P. vivax* or *P. falciparum*) or in a single dosing with a dose of 800 mg (patients affected by with *P. falciparum*) (NCT01753323). The results are published in White et al. (New England Journal of Medicine, 375; 12, 2016). No serious adverse event was reported. The study shows that KAF156 has activity against vivax and falciparum malaria, including artemisinin-resistant parasites. One patient who had received the single 800-mg dose had repeated vomiting and was withdrawn from the study. Five other patients vomited after receiving the single 800-mg dose, as compared with 1 patient with *P. falciparum* malaria in the multiple-dose cohort. Four patients who received the single 800-mg dose reported nausea, as compared with 1 patient with *P. falciparum* malaria in the multiple-dose cohort. Furthermore KAF156 was shown to be rapidly absorbed while having a longer half-life of about 50 hours. Antimalarial drugs that are eliminated rapidly (terminal elimination half-life inferior to 3 days) usually cannot cure falciparum malaria in a single dose.

In view of the foregoing, there is a strong medical need for new therapies for malaria, which is a very common disease responsible of substantial morbidity and mortality. It is desirable to develop new treatment for that disease, including in areas where resistance to ACTs is emerging. Simplifying regimens by developing treatments that can be used in a once daily dose for less than 3-day administration can improve treatment success and reduce probability of developing resistance via improved adherence and thus accelerate malaria eradication.

SUMMARY OF THE INVENTION

The invention addresses these needs by providing novel therapeutic regimen which employ novel new therapeutically effective amounts of an imidazolepiperazine, such as 2-amino-1-(2-(4-fluorophenyl)-3-(4-fluorophenylamino)-8,8-dimethyl-5,6-dihydroimidazo[1,2-a]pyrazin-7(8H)-yl) ethanone (KAF156), or a pharmaceutically acceptable salt thereof; and new dosing regimens of KAF156, that are particularly adequate for short treatment duration and can be used in combination with another anti-malaria partner drug. Disclosed herein is KAF156, or a pharmaceutically acceptable salt thereof, for use in preventing or treating malaria, or delaying the symptoms or ameliorating the conditions associated with malaria, wherein the compound is administered daily at a dose of about 200 mg to about 1000 mg for up to 5 days, e.g. 1 to 3 days, e.g. 1 or 2 days. In particular is disclosed KAF156, or a pharmaceutically acceptable salt thereof, for use in preventing or treating malaria, or delaying the symptoms or ameliorating the conditions associated with malaria, wherein the compound is administered daily at a dose of about 200 mg to about 350 mg for up to 5 days, e.g. 1 to 3 days, e.g. 1 or 2 days.

The invention provides methods of preventing or treating malaria, delaying the symptoms or ameliorating the conditions associated with malaria, comprising daily administering (e.g. once daily) to a subject in need thereof a therapeutically effective amount of an imidazolepiperazine, e.g. 2-amino-1-(2-(4-fluorophenyl)-3-(4-fluorophenylamino)-8,8-dimethyl-5,6-dihydroimidazo[1,2-a]pyrazin-7(8H)-yl) ethanone (KAF156), or a pharmaceutically acceptable salt thereof optionally in combination with another anti-malaria drug, e.g. lumefantrine.

Disclosed herein are methods of preventing or treating malaria, or delaying the symptoms or ameliorating the conditions associated with malaria, comprising daily administering (e.g. once daily) to a subject in need thereof a dose of 2-amino-1-(2-(4-fluorophenyl)-3-(4-fluorophenylamino)-8,8-dimethyl-5,6-dihydroimidazo[1,2-a]pyrazin-7(8H)-yl)ethanone (KAF156), or a pharmaceutically acceptable salt thereof, wherein the dose is of about 200 mg to about 1000 mg and is administered for up to 5 days, e.g. 1 to 3 days, e.g. 1 or 2 days. For example are disclosed methods of preventing or treating malaria, or delaying the symptoms or ameliorating the conditions associated with malaria, comprising daily administering (e.g. once daily) to a subject in need thereof a dose of KAF156, or a pharmaceutically acceptable salt thereof, wherein the dose is of about 200 mg to about 350 mg and is administered for up to 5 days, e.g. 1 to 3 days, e.g. 1 or 2 days.

Disclosed herein are also improved formulations of lumefantrine, e.g. with enhanced bioavailability versus lumefantrine capsules, and the use of such formulations in combination with KAF156, e.g. with specific regimen of KAF156.

In another aspect, the invention provides an imidazolepiperazine, e.g. 2-amino-1-(2-(4-fluorophenyl)-3-(4-fluorophenylamino)-8,8-dimethyl-5,6-dihydroimidazo[1,2-a]pyrazin-7(8H)-yl)ethanone (KAF156), or a pharmaceutically acceptable salt thereof, for use in preventing or treating malaria, or delaying the symptoms or ameliorating the conditions associated with malaria, wherein said imidazolepiperazine, e.g. KAF156, is administered daily (e.g. once daily) at a dose of about 200 mg to about 1000 mg, e.g. for up to 5 days, e.g. for 1 to 3 days. For example, there is provided KAF156, or a pharmaceutically acceptable salt thereof, for use in preventing or treating malaria, or delaying the symptoms or ameliorating the conditions associated with malaria, wherein KAF156 is administered daily (e.g. once daily) at a dose of about 200 mg to about 350 mg, e.g. for up to 5 days, e.g. for 1 to 3 days.

Disclosed herein are doses of KAF156 for use in preventing or treating malaria, to be administered daily (e.g. once daily), of about 200 mg to about 1000 mg, e.g. about 200 mg to about 350 mg (e.g. about 200 mg, about 350 mg, about 400 mg or about 800 mg) of KAF156.

Disclosed herein are pharmaceutical compositions for use in preventing or treating malaria, comprising KAF156, wherein KAF156 is to be administered daily (e.g. once daily) to a patient at a dose of about 200 mg to about 1000 mg, e.g. of about 200 mg to about 350 mg (e.g. about 200 mg, e.g. about 400 mg, e.g. about 800 mg), e.g. for up to 5 days, e.g. for 1 to 5 days, e.g. for 2 to 5 days, e.g. 1 to 3 days, e.g. 1 or 2 days.

Disclosed herein are uses of KAF156 or a pharmaceutically acceptable salt thereof, for the manufacture of a medicament for preventing or treating malaria, characterized in that KAF156 or a pharmaceutically acceptable salt thereof is to be administered daily (e.g. once daily) to a patient at a dose of about 200 mg to about 1000 mg (e.g. about 200 mg, about 350 mg, about 400 mg or about 800 mg), e.g. for up to 5 days, e.g. for 1 to 5 days, e.g. for 2 to 5 days, e.g. 1 to 3 days, e.g. 1 or 2 days.

The invention further provides therapeutic kits for preventing or treating malaria, comprising up to 5 daily doses of KAF156 or a pharmaceutically acceptable salt thereof, wherein the dose of KAF156 or a pharmaceutically acceptable salt thereof is of about 200 mg to about 1000 mg, e.g. of about 200 mg to about 350 mg, e.g. about 200 mg, e.g. about 350 mg, about 400 mg or e.g. about 800 mg.

In some of the above mentioned methods, therapeutic regimens, kits, uses, and pharmaceutical compositions, the imidazolepiperazine, e.g. KAF156 or a pharmaceutically acceptable salt thereof is administered with another anti-malaria drug, e.g. lumefantrine, e.g. as a solid dispersion formulation or microemulsion, e.g. solid dispersion formulation of lumefantrine.

Furthermore the invention provides pharmaceutical combinations comprising i) an imidazolepiperazine, e.g. KAF156 or a pharmaceutically acceptable salt thereof, and ii) another anti-malaria drug, e.g. lumefantrine; and such pharmaceutical combinations for use in preventing or treating malaria, or in delaying the symptoms or ameliorating the conditions associated with malaria. In particular there is provided pharmaceutical combinations comprising about 200 mg to 800 mg of KAF156 and about 400 mg to 1000 mg of lumefantrine. For example, there are provided pharmaceutical combinations comprising about 200 mg to 800 mg of KAF156 and about 400 mg to 1000 mg of lumefantrine, wherein lumefantrin is in form of a solid dispersion formulation or microemulsion, e.g. a solid dispersion formulation.

In particular there are provided fixed combinations of KAF156 and lumefantrine, e.g. of KAF156 and solid dispersion formulation of lumefantrine.

Various (enumerated) embodiments of the disclosure are described herein. It will be recognized that features specified in each embodiment may be combined with other specified features to provide further embodiments of the present disclosure.

Furthermore the invention provides the use of KAF156 for the manufacture of a medicament for treating or preventing malaria, or delaying the symptoms or ameliorating the conditions associated with malaria, wherein the medicament is administered daily (e.g. once daily) during 1 to 5 days, e.g. 1 to 3 days, and comprises about 200 mg to about 1000 mg of KAF156.

For example, there is provided the use of KAF156 for the manufacture of a medicament for treating or preventing malaria, or delaying the symptoms or ameliorating the conditions associated with malaria, wherein the medicament is administered once and comprises about 200 mg, about 350 mg or about 400 mg of KAF156.

For example, there is provided the use of KAF156 for the manufacture of a medicament for treating or preventing malaria, or delaying the symptoms or ameliorating the conditions associated with malaria, wherein the medicament is administered daily (e.g. once daily) for three days and comprises about 200 mg, about 350 mg or about 400 mg of KAF156.

Furthermore the invention provides the use of a combination of KAF156 and lumefantrine, e.g. a fixed dose combination, for the manufacture of a medicament for treating or preventing malaria, or delaying the symptoms or ameliorating the conditions associated with malaria, wherein the medicament is administered daily (e.g. once daily) and comprises about 200 mg of KAF156 and about 480 mg lumefantrine. Lumefantrine may be in form of a solid dispersion formulation.

In one embodiment, there is provided the use of a combination of KAF156 and lumefantrine, e.g. a fixed dose combination, for the manufacture of a medicament for treating or preventing malaria, or delaying the symptoms or ameliorating the conditions associated with malaria, wherein the medicament is administered daily (e.g. once daily) and comprises about 200 mg of KAF156 and about 960 mg lumefantrine. Lumefantrine may be in form of a solid dispersion formulation.

In another embodiment, there is provided the use of a combination of KAF156 and lumefantrine, e.g. a fixed dose combination, for the manufacture of a medicament for treating or preventing malaria, or delaying the symptoms or ameliorating the conditions associated with malaria, wherein the medicament is administered daily (e.g. once daily) and comprises about 400 mg of KAF156 and about 480 mg lumefantrine. Lumefantrine may be in form of a solid dispersion formulation.

In yet another embodiment, there is provided the use of a combination of KAF156 and lumefantrine, e.g. a fixed dose combination, for the manufacture of a medicament for treating or preventing malaria, or delaying the symptoms or ameliorating the conditions associated with malaria, wherein the medicament is administered daily (e.g. once daily) and comprises about 400 mg of KAF156 and about 960 mg lumefantrine. Lumefantrine may be in form of a solid dispersion formulation.

BRIEF DESCRIPTION OF THE DRAWINGS

FIG. 1 discloses the concentration time profiles of lumefantrine following single dose administration of 480 mg dose under fasting conditions as conventional tablet, SDF variant-1 and SDF variant-2 (human study).

DETAILED DESCRIPTION OF THE INVENTION

Figure 2A:
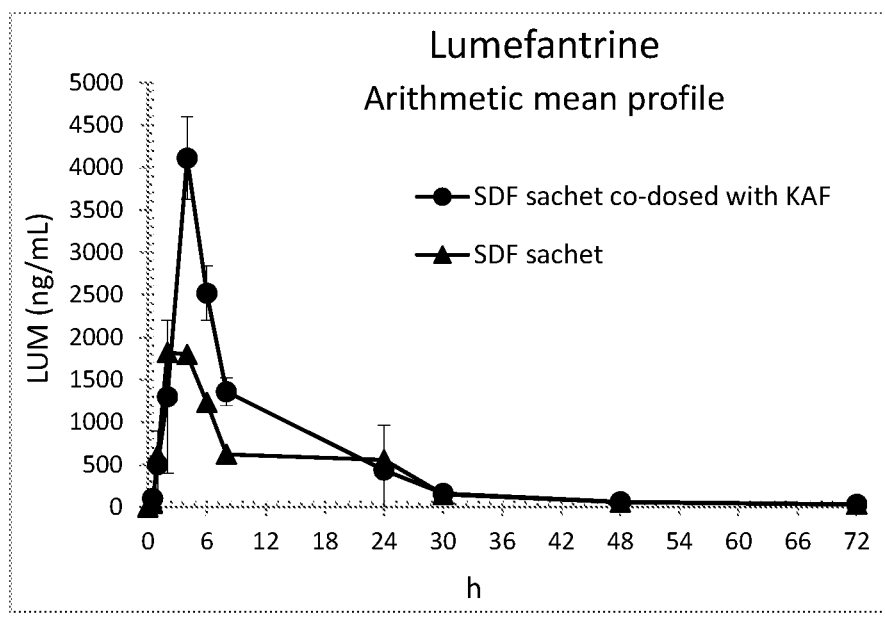
FIGS. 2A and 2B describe Lumeantrine exposure in dog study.

KAF156 (which is 2-amino-1-(2-(4-fluorophenyl)-3-(4-fluorophenylamino)-8,8-dimethyl-5,6-dihydroimidazo[1,2-a]pyrazin-7(8H)-yl)ethanone), is an imidazolepiperazine of formula (i)

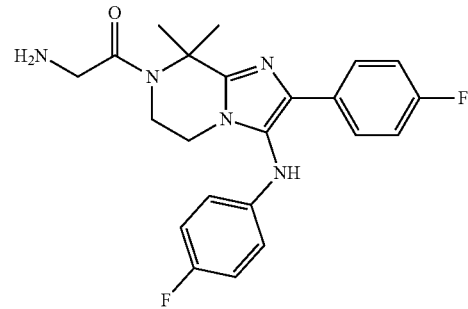 [SMILES: CC1(C)c2nc(-c3ccc(F)cc3)c(Nc3ccc(F)cc3)n2CCN1C(=O)CN]

It is described in WO2011/006143 (example 412).

Various aspects of the disclosure are described in further detail in the following subsections. All patents, published patent applications, publications, references and other material referred to herein are incorporated by reference herein in their entirety.

The term "comprising" encompasses "including" as well as "consisting," e.g. a composition "comprising" X may consist exclusively of X or may include something additional, e.g. X+Y.

According to the invention, treatment of malaria may be prophylactic (to prevent or delay the onset of the disease, or to prevent the manifestation of clinical or subclinical symptoms thereof) or therapeutic suppression or alleviation of symptoms after the manifestation of the disease. Within the meaning of the present invention, the term "treat" also denotes to arrest, delay the onset (i.e., the period prior to clinical manifestation of a disease) and/or reduce the risk of developing or worsening a disease. The term "prevent" or "prevention" refers to a partial or complete inhibition of development or progression of the disease.

As used herein malaria refers to the diseases induced by *Plasmodium falciparum, Plasmodium vivax, Plasmodium ovale* or *Plasmodium* malaria, e.g. acute and cerebral malaria, e.g. uncomplicated *P. falciparum* malaria.

The term "an effective amount" or "therapeutically effective amount" of an imidazolepiperazine, e.g. KAF156 or a pharmaceutically acceptable salt thereof, refers to an amount of the imidazolepiperazine, e.g. KAF156 or a pharmaceutically acceptable salt thereof that will elicit a biological or medical response in a patient, for example, reduction or inhibition of a protein activity, or ameliorate symptoms, alleviate conditions, slow or delay disease progression, or prevent a disease, etc. The term "effective amount" or "therapeutically effective amount" is defined herein to refer to an amount sufficient to provide an observable improvement over the baseline clinically observable signs and symptoms of the condition treated.

The term "about" or "approximately" shall have the meaning of within 10%, more preferably within 5%, of a given value or range.

The term "pharmaceutically acceptable" means a non-toxic material that does not interfere with the effectiveness of the biological activity of the active ingredient(s).

The term "daily" refers to administering the drug, e.g. KAF156, lumefantrine, or the pharmaceutical combination comprising KAF156 and lumefantrine, in a daily manner, i.e. every day. It can correspond to a unique administration (once daily, also referred as QD) or several administrations a day, such as up to four times a day.

Preferably KAF156 is administered once a day administration. Similarly lumefantrine is preferably administered once a day.

According to the invention, KAF156 (in form of a free base) is administered at a dose comprised between about 200 mg and about 800 mg, e.g. between about 200 mg and about 600 mg, e.g. between about 200 mg and about 500 mg, e.g. between about 250 mg and about 500 mg, e.g. between about 250 mg and about 450 mg, e.g. between about 200 mg and about 400 mg. For example, KAF156 (in form of a free base) is administered at a dose of about 200 mg, about 250 mg, about 300 mg, about 400 mg, about 450 mg, about 500 mg, about 550 mg, or about 600 mg, about 650 mg, about 700 mg, about 750 mg, about 800 mg. In specific embodiments, these doses are for daily administration, e.g. are daily doses. In other embodiments, these doses are for once daily administration.

In some embodiments, there are provided new therapeutic regimens of KAF156 for use in preventing or treating malaria, comprising administering (e.g. daily) a dose of KAF156 of about 200 mg to about 900 mg, e.g. about 200 mg to about 800 mg, e.g. about 200 mg to about 600 mg, e.g. about 200 mg to about 500 mg, e.g. about 250 mg to about 500 mg, e.g. about 250 mg to about 450 mg, e.g. about 200 mg to about 400 mg.

For example, the therapeutic regimens of KAF156 for use in preventing or treating malaria, comprise administering (e.g. daily) a dose of KAF156 of about 200 mg, 250 mg, about 300 mg, about 400 mg, about 450 mg, about 500 mg, about 550 mg, or about 800 mg.

According to the invention, KAF156 or a pharmaceutically acceptable salt thereof, is administered daily during up to 5 days, e.g. for 1 to 5 days, e.g. for 1 to 3 days, e.g. for 2 to 5 days, e.g. for 1 or 2 days, e.g. for one day. In specific embodiments, there is provided a dose of KAF156 or a pharmaceutically acceptable salt thereof for unique administration, e.g. unique daily administration.

Provided herein are therapeutic kits for use in preventing or treating malaria, comprising KAF156 or a pharmaceutically acceptable salt thereof, e.g. doses thereof to be administered daily. Additionally, such kits may comprise means for administering the imidazolepiperazine, e.g. KAF156 and instructions for use. These kits may contain one (or more) additional anti-malaria agent(s), e.g. lumefantrine.

Accordingly, disclosed herein are therapeutic kits comprising: a) a pharmaceutical composition comprising a therapeutically effective amount of an imidazolepiperazine, e.g. KAF156 or a pharmaceutically acceptable salt thereof; b) means for administering the imidazolepiperazine or a pharmaceutically acceptable salt thereof (KAF156) to a patient at risk of or having malaria; and c) instructions providing administering the imidazolepiperazine (e.g. KAF156) to the patient up to five days.

In other embodiments are provided therapeutic kits comprising a) a pharmaceutical composition comprising a doses of an imidazolepiperazine, e.g. KAF156 or a pharmaceutically acceptable salt thereof, e.g. about 200 mg to about 1000 mg, e.g. about 200 mg, e.g. about 400 mg or e.g. about 800 mg; b) means for administering the imidazolepiperazine or a pharmaceutically acceptable salt thereof (KAF156) to a patient at risk of or having malaria; and c) instructions providing administering the imidazolepiperazine (e.g. KAF156) to the patient.

In some embodiments the therapeutic kit comprises doses of the imidazolepiperazine, e.g. KAF156 or a pharmaceutically acceptable salt thereof, e.g. KAF156, for daily administration during up to 5 days, e.g. 1 to 5 doses, e.g. 2 to 5 doses, e.g. 1 to 3 doses, e.g. 1 to 2 doses, e.g. one dose. Such doses can be of about 200 mg to about 1000 mg, e.g. about 200 mg, e.g. about 300 mg, e.g. about 305 mg, e.g. about 400 mg or e.g. about 800 mg of KAF156 (as free base).

For example, there are provided therapeutic kits comprising one to five doses of KAF156, or a pharmaceutically acceptable salt thereof, for daily administration, wherein said doses are of about 200 mg to about 1000 mg, e.g. about 200 mg, e.g. about 300 mg, about 350 mg, e.g. about 400 mg or e.g. about 800 mg of KAF156 (as free base).

In some of the above mentioned methods, therapeutic regimens, kits, uses, and pharmaceutical compositions, the imidazolepiperazine, e.g. KAF156 or a pharmaceutically acceptable salt thereof is administered with another anti-malaria drug, e.g. lumefantrine.

According to the invention, the treatment, e.g. KAF156 or a combination of KAF156 with another anti-malaria agent, should provide adequate parasiticidal serum levels over a period of at least 6-7 days (3 parasite life-cycles approximately) in order to achieve curing the patient.

Accordingly there are provided pharmaceutical combinations comprising i) an imidazolepiperazine, e.g. KAF156 or a pharmaceutically acceptable salt thereof, e.g. KAF156, and ii) another anti-malaria agent, e.g. lumefantrine.

In some embodiments, there are provided pharmaceutical combinations comprising KAF156, and ii) another anti-malaria agent, for use in preventing or treating malaria, wherein KAF156 (as a free base) is to be administered daily at a dose of about 200 mg to about 1000 mg, e.g. about 200 mg to about 900 mg, e.g. about 200 mg to about 800 mg, e.g. about 200 mg to about 600 mg, e.g. about 200 mg to about 500 mg, e.g. about 200 mg to about 350 mg, e.g. about 200 mg to about 300 mg, e.g. about 250 mg to about 500 mg, e.g. about 250 mg to about 450 mg, e.g. about 250 mg to about 350 mg, e.g. about 200 mg to about 400 mg, e.g. about 300 mg to about 400 mg.

For example there are provided pharmaceutical combinations comprising i) daily doses of KAF156, and ii) another anti-malaria agent, for preventing or treating malaria, wherein the dose of KAF156 (as free base) is about 200 mg, about 250 mg, about 300 mg, about 350 mg, about 400 mg, about 450 mg, about 500 mg, about 550 mg, or about 800 mg.

In some embodiments, the second anti-malaria agent is selected from the group consisting of proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine and pyronaridine.

In particular, the second anti-malaria agent is lumefantrine.

Lumefantrine may be in the form of as a solid dispersion formulation.

According to the invention, lumefantrine is to be administered daily at a dose of about 400 mg to 1000 mg, e.g. about 400 mg to about 500 mg, e.g. about 900 mg to about 1000 mg. For example, lumefantrine is to be administered daily at a dose of about 480 mg or about 960 mg.

According to the invention, imidazolepiperazine, e.g. KAF156 or a pharmaceutically acceptable salt thereof, e.g. KAF156, can be administered prior to, simultaneously with, or after the second anti-malaria agent, e.g. lumefantrine.

The terms "co-administration" or "combined administration" or the like as utilized herein are meant to encompass administration of i) an imidazolepiperazine, e.g. KAF156 or a pharmaceutically acceptable salt thereof, e.g. KAF156, and ii) the second anti-malaria agent, e.g. lumefantrine, to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, i.e. the imidazolepiperazine and the second anti-malaria agent, e.g. KAF156 and lumefantrine, are both administered to a patient simultaneously in the form of a single entity or dosage. The term "non-fixed combination" means that the active ingredients, i.e. the imidazolepiperazine and the second anti-malaria agent, e.g. KAF156 and lumefantrine, are both administered to a patient as separate entities either simultaneously, concurrently or sequentially with no specific time limits, wherein such administration provides therapeutically effective levels of the two compounds in the body of the patient.

In general, the imidazolepiperazine, e.g. KAF156 or a pharmaceutically acceptable salt thereof will be administered via any of the usual and acceptable modes known in the art.

The imidazolepiperazine, e.g. KAF156 can be administered as pharmaceutical compositions by any conventional route, in particular enterally, e.g. orally, e.g. in the form of tablets or capsules, or parenterally, e.g. in the form of injectable solutions or suspensions, topically, e.g. in the form of lotions, gels, ointments or creams, or in a nasal or suppository form. Pharmaceutical compositions comprising the imidazolepiperazine, e.g. KAF156, optionally in combination with a second anti-malaria agent, e.g. lumefantrine, in association with at least one pharmaceutically acceptable carrier or diluent can be manufactured in a conventional manner by mixing, granulating or coating methods. For example, oral compositions can be tablets or gelatin capsules comprising the imidazolepiperazine, e.g. KAF156, together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g. starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g. to the skin and eyes, are preferably aqueous solutions, ointments, creams or gels well known in the art. Such may contain solubilizers, stabilizers, tonicity enhancing agents, buffers and preservatives.

According to the invention, lumefantrine can be prepared as a solid dispersion. The term solid dispersion refers to dispersion of an active molecule in an inert carrier in the solid state prepared by solvent, melting or solvent-melting methods.

Said compositions can be prepared using different processes e.g. solvent evaporation, spray drying, melt extrusion, fluid bed granulation technology, solvent evaporation, use of polymers, melt cooling. The techniques that can be used are known to the one skilled in the art, and are described e.g. in Gahoi et al (Int. J Pharm Sci. Rev. Res. 8 (2), 170-175. 2011), Balaji et al (International Journal of Pharmacy and Pharmaceutical Sciences, Vol 6 Issue 2, 2014), Fule et al (Int. J. drug del. 4, 2012, 95-106). The solid dispersion can further be mixed with other excipients and can be formulated into capsule or tablet dosage forms. Excipients that can be used can be e.g. poloxamer 188 (e.g. in higher amount than the drug, e.g. four times more than the drug amount of drug); poloxamer 407, PEG800, solutol, gelucire, Polyvinylpyrollidone (PVP) (e.g. PVP K30) or basic butylated methacrylate copolymer (e.g. Eudragit EPO). Preferably, the solid dispersion of lumefantrine comprises excipients selected from the group consisting of Solupus, Eudragit EPO, PVP K30 and mixture thereof, e.g. selected from the group consisting of Eudragit EPO, PVP K30 and mixture thereof.

The term solid dispersion refers to a group of solid products consisting of at least two different components, generally a hydrophilic matrix and a hydrophobic drug. Herein is described the preparation of solid dispersions using hydrophilic carriers, such as e.g. polyvinylpyrrolidone (Povidone, PVP), polyethylene glycols (PEG 6000), Surfactants like Tween-80, Poloxamer, and Sodium Lauryl Sulphate (SLS).

According to the invention, lumefantrine can be prepared as a microemulsion, e.g. as described in Patel (DARU J. Pharm. Sci, 21 (27), 2013).

According to the invention, lumefantrine can be in amorphous state.

According to the invention, there are provided pharmaceutical combination comprising about 200 mg of KAF156 (as free base), and about 400 mg to 500 mg of lumefantine (as free base), e.g. about 480 mg lumefantrine (as free base), for daily administration.

According to the invention, there are provided pharmaceutical combination comprising about 300 mg or 350 mg of KAF156 (as free base), and about 400 mg to 500 mg of lumefantine (as free base), e.g. about 480 mg lumefantrine (as free base), for daily administration.

According to the invention, there are provided pharmaceutical combination comprising about 400 mg of KAF156 (as free base) and about 400 mg to 500 mg of lumefantine (as free base), e.g. about 480 mg lumefantrine (as free base), for daily administration.

According to the invention, there are provided pharmaceutical combination comprising about 800 mg of KAF156 (as free base) and about 400 mg to 500 mg of lumefantine (as free base), e.g. about 480 mg lumefantrine (as free base), for daily administration.

According to the invention, there are provided pharmaceutical combination comprising about 200 mg of KAF156 (as free base) and about 900 mg to 1000 mg of lumefantine (as free base), e.g. about 960 mg lumefantrine (as free base), for daily administration.

According to the invention, there are provided pharmaceutical combination comprising about 300 mg or 350 mg of KAF156 (as free base) and about 900 mg to 1000 mg of lumefantine (as free base), e.g. about 960 mg lumefantrine (as free base), for daily administration.

According to the invention, there are provided pharmaceutical combination comprising about 400 mg of KAF156 (as free base) and about 900 mg to 1000 mg of lumefantine (as free base), e.g. about 960 mg lumefantrine (as free base), for daily administration.

According to the invention, the pharmaceutical combinations comprising KAF156 and lumefantine (e.g. as described hereinabove) are fixed dose combinations. In such a fixed dose combination, lumefantrine can be formulated as a solid dispersion formulation.

It is understood that the examples and embodiments described herein are for illustrative purposes only and that various modifications or changes in light thereof will be suggested to the persons skilled in the art and are to be included within the spirit and purview of this application and scope of the appended claims. All publications, patents, and patent applications cited herein are hereby incorporated by reference for all purposes.

EXAMPLES

Example 1: Lumefantrine Solid Dispersion Capsule Composition

| Ingredient | mg/unit | % w/w |
| --- | --- | --- |
| Lumefantrine drug substance | 75.000 | 18.75 |
| Polyvinylpyrrolidone K30 | 120.000 | 26.25 |
| Eudragit EPO | 105.000 | 26.25 |
| Croscarmellose sodium | 64.000 | 16.00 |
| Microcrystalline cellulose | 30.000 | 7.50 |
| Poloxamer 188 | 15.000 | 3.75 |
| Colloidal Silicon dioxide | 4.000 | 1.00 |
| Magnesium stearate | 2.000 | 0.50 |
| Total capsule fill | 400.000 | 100.00 |

Example 2: Lumefantrine Solid Dispersion (SD) Capsule Composition

| Ingredient | mg/unit | % w/w |
| --- | --- | --- |
| Lumefantrine drug substance | 75.000 | 18.75 |
| Polyvinylpyrrolidone K30 | 120.000 | 30.00 |
| Eudragit EPO | 105.000 | 26.25 |
| Croscarmellose sodium | 64.000 | 16.00 |
| Microcrystalline cellulose | 30.000 | 7.50 |
| Colloidal Silicon dioxide | 4.000 | 1.00 |
| Magnesium stearate | 2.000 | 0.50 |
| Total capsule fill | 400.00 | 100.00 |

The compositions of Examples 1 and 2 have shown significantly higher dissolution at pH 1 and pH2 in presence and in absence of a surfactant.

Example 3: Lumefantrine Microemulsion Composition

| Ingredient | mg/unit | % w/w |
| --- | --- | --- |
| Lumefantrine drug substance | 150.000 | 10.00 |
| Oleic acid | 596.700 | 39.78 |
| Cremophore EL | 596.700 | 39.78 |
| Triethylcitrate | 149.100 | 9.94 |
| Butylated hyroxytoluene | 7.500 | 0.50 |
| Total | 1500.000 | 100.00 |

As can be seen in the table below, the presence of butylated hydroxytoluene as a stabilizer at a level of 0.5% has resulted in significant improvement in the stability of the microemulsions which is evident by the decreased levels of Lumefantrine step-4 impurity.

Stability data at 4 week time point for microemulsion

| Condition | Microemulsion with butylated Hydroxyltoluene | | Microemulsion without butylated hydroxyltoluene | |
| --- | --- | --- | --- | --- |
| | Assay (%) | Lumefantrine step-4 (%) | Assay (%) | Lumefantrine step-4 (%) |
| Initial | 101.9 | 0.18 | 103.6 | 0.00 |
| 5° C. | 87.5 | 0.00 | 75.4 | 27.42 |

-continued

| Condition | Microemulsion with butylated Hydroxyltoluene | | Microemulsion without butylated hydroxyltoluene | |
|---|---|---|---|---|
| | Assay (%) | Lumefantrine step-4 (%) | Assay (%) | Lumefantrine step-4 (%) |
| 25° C., 60% R.H | 94.4 | 0.00 | 62.5 | 32.24 |
| 50° C., 75% R.H | 74.6 | 0.22 | 59.7 | 19.04 |

Example 4

Bioavailability of the solid dispersion capsule formulation was assessed in male beagle dogs along with the conventional tablet (composition/process similar to Coartem®) and microemulsion.

Formulation tested in dogs:

| Formulation | Dosing information for administration of 150 mg |
|---|---|
| Tablet[1] | Lumefantrine 150 mg tablet |
| Solid dispersion capsules[2] | Lumefantrine 7 mg HGC (2 capsules to be administered) |
| Microemulsion | Lumefantrine 10% w/w microemulsion (1.5 g microemulsion contains 150 mg lumefantrine) |

[1]Composition/process similar to Coartem ®
[2]Corresponds to the composition of example 2.

The plasma profile and pharmacokinetic parameters (table below) from this study showed almost 4 fold and 9 fold higher Lumefantrine exposure from solid dispersion capsule and microemulsion in comparison to the conventional tablet. Lumefantrine-SD capsule has an improved absorption profile and less food effect, leading to exposure which allows for a once-daily regimen.

Lumefantrine Pharmacokinetics (PK) Data from the Dog Study:

| Formulation | Cmax (ng/ml) | $AUC_{last}$ (μg · h/ml) | $AUC_{inf}$ (μg · h/ml) | $T_{max}$ (h) |
|---|---|---|---|---|
| Tablet | 1580 ± 491 | 10.2 ± 7.8 | 14.8 ± 4.65 | 4 (2-4) |
| Solid dispersion Capsule [1] | 3380 ± 2380 | 41.7 ± 31.6 | 43.1 ± 32.7 | 6 (4-6) |
| Microemulsion [2] | 9720 ± 4000 | 89.1 ± 46 | 91.3 ± 46.7 | 4 (2-4) |

[1] Corresponds to the composition of example 2.
[2] Corresponds to the composition of example 3.

Example 5

The pharmacokinetics of the two SD capsule variants described in Examples 1 and 2 above (that both contain lumefantrine in amorphous form) was assessed in a randomized, open-label, sequential two-parts study in healthy volunteers. In Part 1, relative bioavailability of the two SDF variants was compared with conventional formulation (120 mg conventional tablet) after single dose administration of 480 mg under fasted conditions in three parallel cohorts.

An interim internal review was conducted after approximately 12 subjects from each cohort had completed study (Day 12) to determine if the lumefantrine SD capsules variants met protocol specified criterion (enhanced lumefantrine bioavailability >4 fold) to continue into Part 2.

In Part 2, which followed a washout period of 5 weeks, the same subjects were reallocated to a 480 mg food effect arm or a higher dose arm (960 mg dose) in a 1:1 ratio. After dosing, subjects were followed for 12 days (Days 53-64) before a final end-of-study (EOS) visit by Day 71 (approximately).

For fasting treatments, subjects had no food or liquid (except water) for at least 10 hours prior to administration of study drug and continued to fast for at least 4 hours post dose. For the fed treatments, subjects were provided a high fat breakfast (total of 916 calories with 178, 241, and 497 calories from protein, carbohydrate, and fat, respectively). The meal was served and consumed within 30 minutes and study drug was administered within 5 minutes after completion of the meal. All doses were administered with 180-240 mL water.

The study population comprised healthy male subjects of at least 50 kg in weight (BMI within 18.0-30.0 kg/m2). A total of 49 male subjects (18-44 years) were randomized into Part 1 of the study and of these, 16 subjects continued into Part 2 of the study.

Pharmacokinetic (PK) Assessment:

All blood samples were taken by either direct venipuncture or an indwelling cannula inserted in a forearm vein. PK samples were obtained and evaluated in all subjects at all dose levels. Blood samples for PK analysis of lumefantrine were collected at pre-dose and 1, 2, 4, 5, 6, 8, 10, 12, 24, 36, 48, 72, 120, 168, 216, and 264 hours post-dose.

Lumefantrine concentration was determined by a validated Liquid chromatography-Mass spectrometry (LC-MS/MS) method with a Lower Limit of Quantification (LLOQ) of 50 ng/mL. Briefly, the bioanalytical method consisted of protein precipitation followed by solid phase extraction of human plasma samples and analysis of diluted samples by LC-MS/MS in Multiple Reaction Monitoring (MRM) positive mode using Electrospray Ionization (ESI) as the ionization technique. The lower and upper limits of quantification for linear range were 50.0 ng/mL and 20000 ng/mL respectively using 10 μL of human plasma. Lumefantrine in human plasma is stable for 44 hours at room temperature; 9 months at <−70° C.; 3 freeze/thaw cycles at <−70° C. The extract is stable for 100 hours in an autosampler at 8° C. The stability data could cover the period from sampling to analysis of all study samples. For eight points calibration concentrations (50, 100, 200, 500, 2000, 5000, 16000 and 20000 ng/mL) bias was within the range of ±15.0% at all concentrations except for LLOQ (50 ng/mL) for which it was within the range of ±20.0%. For quality control samples (150 ng/mL, 2500 ng/mL and 15000 ng/mL) bias was within the range of ±15.0% for at least ⅔ of the individual values.

Concentrations below the LLOQ were considered as "zero" for pharmacokinetic analysis. The following pharmacokinetic parameters were determined from the plasma concentration-time data by non-compartmental analysis in Phoenix WinNonlin (Version 6.4): $C_{max}$, $T_{max}$, $AUC_{0-72\ h}$, $AUC_{last}$, $AUC_{inf}$, $T_{1/2}$, Vz/F and CL/F. The linear trapezoidal rule was used for AUC calculation.

Statistical Methods:

Sample size: Part 1: 36 subjects (12 per cohort) had complete data from each cohort for which would allow adequate detection of at least a 1.5-fold change. For the observed ratios from 1.5 to 5.0-fold change the predicted 90% confidence intervals for the primary pharmacokinetic parameter ratio ($AUC_{inf}$, $AUC_{last}$ and $C_{max}$ based on log transformation) are: 1.5 (1.08, 2.09), 2.0 (1.44, 2.78), 3.0 (2.15, 4.18), 4.0 (2.87, 5.57), 5.0 (3.59, 6.96) using the historic data on variability. In Part 2, no formal statistical calculations were considered in calculating the sample size.

The log transformed primary pharmacokinetic parameters $C_{max}$, $AUC_{last}$ and $AUC_{inf}$ were analyzed separately by using a linear effects model with treatment as fixed effects. The estimated mean and 90% confidence intervals of treatment difference were back transformed to obtain the geometric mean ratio and 90% confidence intervals of the ratio and those were reported to represent the relative bioavailability of SD formulation(s) variant-1 vs. conventional tablet and SDF variant-2 vs. conventional tablet.

To assess the pharmacokinetics of higher single dose of 960 mg in comparison to single dose of 480 mg log transformed primary pharmacokinetic Parameters ($C_{max}$, $AUC_{last}$ and $AUC_{inf}$) were compared using fixed effects model with treatment and subject as fixed effects. The estimated mean and 90% confidence intervals of treatment difference were back transformed to obtain the geometric mean ratio and 90% confidence intervals of the ratio and those were reported to represent the exposure of SD formulation(s) at 960 mg single dose strength, using 480 mg dose as reference.

An exploratory assessment of food effect between fasted and fed treatments were evaluated for log transformed primary pharmacokinetic parameters ($C_{max}$, $AUC_{last}$ and $AUC_{inf}$) using a fixed effects model with treatment and subject as fixed effects. The estimated mean and 90% confidence intervals of treatment difference were back transformed to obtain the geometric mean ratio and 90% confidence intervals of the ratio and those were reported to represent the relative bioavailability under fed conditions relative to fasted condition.

Results:

The concentration time profiles of lumefantrine following single dose administration of 480 mg dose under fasting conditions as conventional tablet, SDF variant-1 and SDF variant-2 are presented in FIG. 1. Summary pharmacokinetic parameters corresponding to FIG. 1 are presented in Table below:

| Parameter (unit) # | Cohort 1 (480 mg conventional tablets, fasting) N = 16 | Cohort 2 (480 mg SD variant-1 capsules, fasting) N = 16 | Cohort 3 (480 mg SD variant-2 capsules, fasting) N = 16 | Cohort 4 (480 mg SD variant-1 capsules, fed) N = 4 | Cohort 6 (480 mg SD variant-2 capsules, fed) N = 4 | Cohort 5 (960 mg SD variant-1 capsules, fasting) N = 4 | Cohort 7 (960 mg SD variant-2 capsules, fasting) N = 4 |
|---|---|---|---|---|---|---|---|
| $C_{max}$ (ng/mL) | 260 ± 143 [55.0] (n = 16) | 4790 ± 1680 [35.0] (n = 16) | 3780 ± 2130 [56.5] (n = 16) | 29700 ± 10900 [36.8] (n = 3) | 19800 ± 346 [1.7] (n = 3) | 8410 ± 3970 [47.2] (n = 4) | 7280 ± 2180 [30.0] (n = 3) |
| $AUC_{last}$ (h × µg/mL) | 3.08 ± 2.66 [86.2] (n = 16) | 112 ± 48.9 [43.8] (n = 13) | 70.7 ± 50.6 [71.6] (n = 15) | 568 ± 183 [32.3] (n = 4) | 477 ± 76.2 [16.0] (n = 3) | 187 ± 117 [62.4] (n = 3) | 121 ± 77.6 [64.2] (n = 4) |
| $AUC_{inf}$ (h × µg/mL) | 7.15 ± 2.27 [31.7] (n = 6) | 117 ± 48.6 [41.6] (n = 15) | 82.2 ± 50.8 [61.8] (n = 15) | 599 ± 206 [34.3] (n = 4) | 496 ± 66.2 [13.3] (n = 4) | 219 ± 113 [51.8] (n = 4) | 129 ± 83.5 [64.8] (n = 4) |
| $AUC_{0-24\ h}$ (h × µg/mL) | 2.80 ± 1.89 [67.3] (n = 16) | 57.6 ± 22.9 [39.7] (n = 16) | 42.8 ± 24.9 [58.0] (n = 16) | 290 ± 96.7 [33.4] (n = 4) | 261 ± 21.3 [8.2] (n = 4) | 107 ± 52.0 [48.8] (n = 4) | 71.9 ± 38.9 [54.1] (n = 4) |
| $AUC_{0-72\ h}$ (h × µg/mL) | 3.51 ± 2.74 [77.9] (n = 16) | 87.1 ± 35.6 [40.8] (n = 16) | 61.8 ± 37.3 [60.3] (n = 16) | 435 ± 142 [32.7] (n = 4) | 388 ± 39.7 [10.2] (n = 4) | 162 ± 81.0 [50.1] (n = 4) | 104 ± 60.0 [57.7] (n = 4) |
| $T_{max}$(h) | 6.00 (5.00-10.0) (n = 16) | 6.00 (6.00-10.0) (n = 16) | 6.00 (6.00-10.0) (n = 16) | 6.00 (6.00-8.00) (n = 3) | 8.00 (5.00-8.03) (n = 3) | 8.00 (6.00-10.0) (n = 4) | 6.00 (6.00-10.0) (n = 3) |
| T½ (h) | 14.2 ± 5.17 [36.5] (n = 6) | 76.5 ± 27.3 [35.6] (n = 15) | 53.0 ± 38.3 [72.2] (n = 15) | 73.7 ± 15.5 [21.0] (n = 4) | 94.2 ± 30.2 [32.0] (n = 4) | 115 ± 46.7 [40.6] (n = 4) | 58.1 ± 44.8 [77.2] (n = 4) |
| CL/F (L/h) | 71.9 ± 18.4 [25.5] (n = 6) | 5.53 ± 4.72 [85.3] (n = 15) | 7.95 ± 4.52 [56.8] (n = 15) | 0.869 ± 0.266 [30.6] (n = 4) | 0.980 ± 0.121 [12.4] (n = 4) | 5.37 ± 2.60 [48.5] (n = 4) | 10.9 ± 7.66 [70.3] (n = 4) |
| Vz/F (L) | 1360 ± 259 [19.0] (n = 6) | 500 ± 190 [38.1] (n = 15) | 444 ± 120 [27.0] (n = 15) | 88.2 ± 12.2 [13.8] (n = 4) | 135 ± 54.3 [40.4] (n = 4) | 824 ± 366 [44.4] (n = 4) | 625 ± 133 [21.3] (n = 4) | n = number of subjects with non-missing values within the parameter

All values are presented as mean ± SD[CV %] (n), except $T_{max}$ which is presented as median (range).

Irrespective of the formulation, lumefantrine was absorbed with median $T_{max}$ of 6 hours with some initial lag time.

The geometric mean ratios and 90% CIs for $C_{max}$, $AUC_{last}$ and $AUC_{inf}$ for both SD formulations variant-1 and variant-2 relative to the conventional tablet (Reference) are presented in Table below.

| Parameter | Treatment | N* | Adjusted Geo-mean | Comparison | Treatment Comparison Geo-mean ratio | (90% CI) |
|---|---|---|---|---|---|---|
| $AUC_{inf}$ (h × µg/mL) | Cohort 1 | 6 | 6.90 | | | |
| | Cohort 2 | 15 | 104.46 | Cohort 2 vs Cohort 1 | 15.15 | (9.79, 23.44) |
| | Cohort 3 | 15 | 70.12 | Cohort 3 vs Cohort 1 | 10.17 | (6.57, 15.73) |
| $AUC_{last}$ (h × µg/mL) | Cohort 1 | 16 | 2.02 | | | |
| | Cohort 2 | 13 | 97.47 | Cohort 2 vs Cohort 1 | 48.19 | (26.02, 89.23) |
| | Cohort 3 | 15 | 49.07 | Cohort 3 vs Cohort 1 | 24.26 | (13.41, 43.90) |
| $C_{max}$ (ng/mL) | Cohort 1 | 16 | 224.50 | | | |
| | Cohort 2 | 16 | 4376.88 | Cohort 2 vs Cohort 1 | 19.50 | (13.12, 28.97) |
| | Cohort 3 | 16 | 3014.73 | Cohort 3 vs Cohort 1 | 13.43 | (9.04, 19.96) |

The log transformed primary pharmacokinetic parameters of $C_{max}$, $AUC_{last}$ and $AUC_{inf}$ were analyzed separately by using a linear mixed effects model with treatment (cohort) as fixed effect.

n*=number of subjects with non-missing values
Reference: Cohort 1: 480 mg conventional tablets (Fasting)
Test-1: Cohort 2: 480 mg SD variant-1 capsules (Fasting)
Test-2: Cohort 3: 480 mg SD variant-2 capsules (Fasting)

The rate and extent of absorption of lumefantrine from both the SD formulations was enhanced significantly relative to conventional formulation. The $C_{max}$ for SD formulation variant-1 was 47.9 µg/mL. The $C_{max}$ for SD formulation variant-1 and SD formulation variant-2 was about 19-fold and about 13-fold higher respectively, compared to conventional formulation under fasting conditions.

The bioavailability (through $AUC_{last}$) of lumefantrine from SD formulation variant-1 and variant-2 increased up to about 48-fold and about 24-fold, respectively, relative to conventional formulation.

Furthermore, both variants demonstrated positive food effect and less than proportional increase in exposure between 480 mg and 960 mg doses. The SD formulations achieved considerable increase in bioavailability without the need to be administered with food rich in fat.

The results show that SD formulation enhances lumefantrine bioavailability to a significant extent.

Example 6

The study design is described in the table below. To stimulate gastric secretion, each animal (dog) received a single 6-µg/kg intramuscular injection of pentagastrin approximatively 60 minutes prior to test article administration. Washout between each treatment was approximatively 7-8 days.

| Phase/ Group | Number of Male Animals | Test Article | Dose Route | Target Dose Level (mg/animal) | Target Dose Volume (mL/animal) |
|---|---|---|---|---|---|
| 1/1 | 3 | Lumefantrine suspension (updated variant SD) | Oral | 150[a] | 40 |
| 2/1 | 3 | Luinefantrine-SDF sachet and KAF156 tablet (FCT) | Oral | 15[b] and 100[c] | 5[bd] and 1[cf] |
| 3/1 | 3 | Luniefantrine-SDF capsule | Oral | 150[e] | 2[eg] |
| 4/1 | 3 | Lumefantrine-SDF sachet | Oral | 15[b] | 5[bd] |
| 5/1 | 3 | KAF156 tablet (FCT) | Oral | 100[c] | 1[cf] |

[a]Lumefantrine suspension dose is 600 mg (containing 25% drug load) in 40 mL/animal or 150 mg/animal Lumefantrine.

[b]Lumefantrine-SD sachet suspension dose is 3.37 g (containing 17.78% drug load) in 199 mL vehicle (or 16.9 mg/mL) and will be dosed at 3 mg/mL (LUM566), 15 mg/kg, and 5 mL/kg.

[c]The dose of KAF156 will be 100 mg (1 × 100 mg).

dUnits are mL/kg.

[e]The dose of Lumefantrine will be 150 mg (2 × 75 mg capsules).

[f]Units are tablets/animal.

[g]Units are capsules/animal.

Figure 2B:
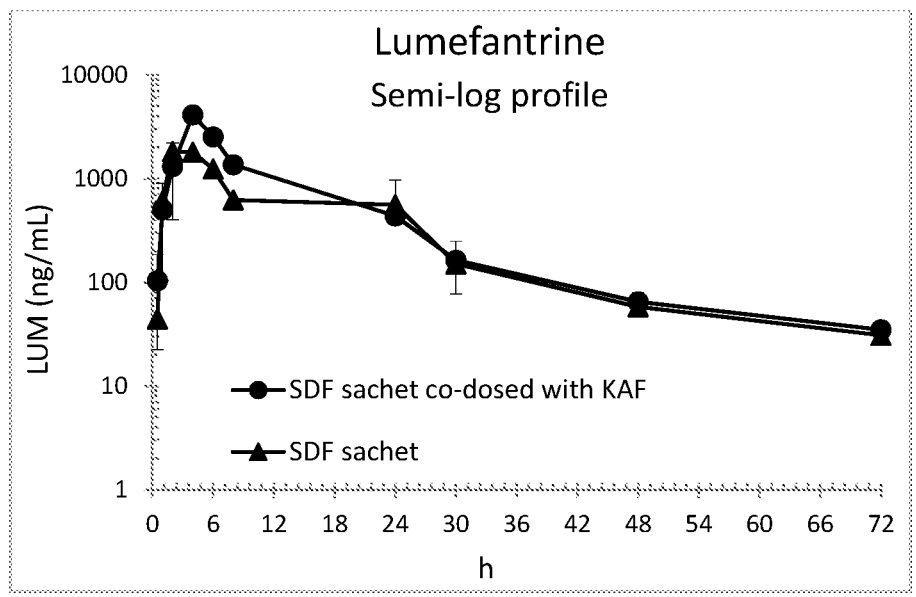

The pharmacokinetic data of lumefantrine are presented in the table below:

The results as indicated in the table above and in FIGS. 2A and 2B show that lumefantrine exposure is increased by around 1.5 fold when administered together with KAF156.

Figure 3A:
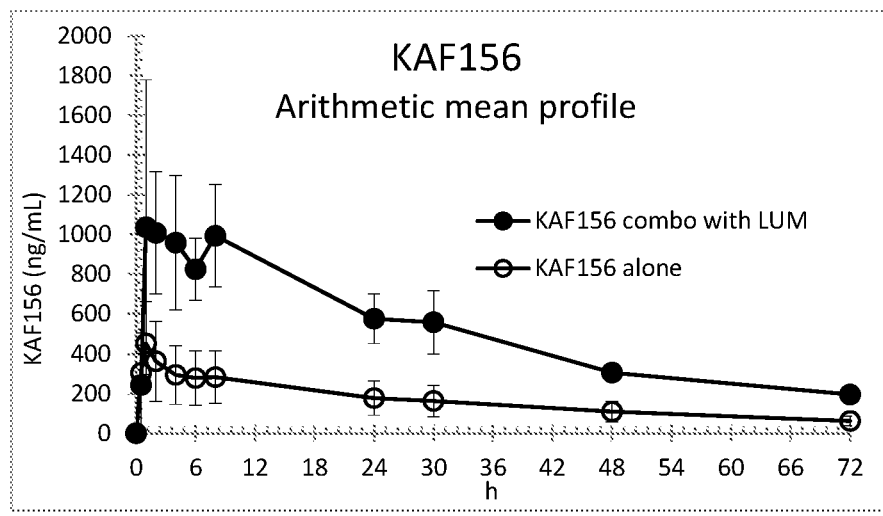
FIGS. 3A and 3B describe KAF156 exposure in dog study.
Figure 3B:
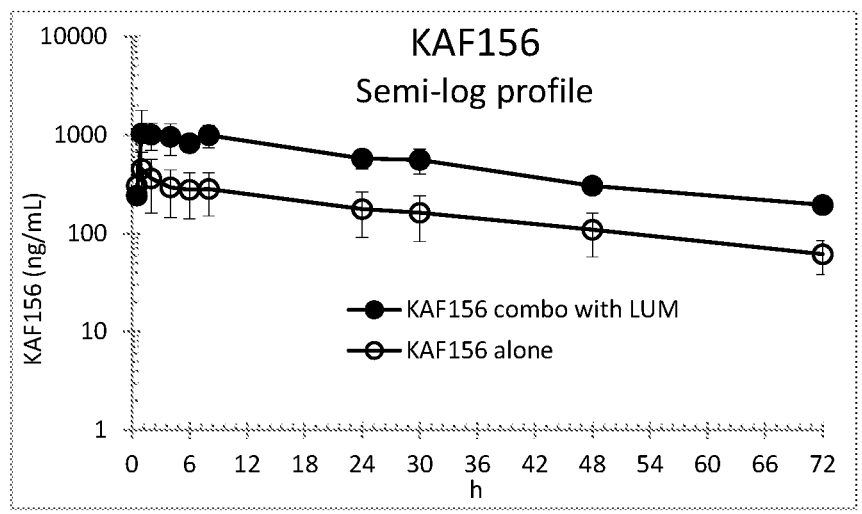

Unanticipatedly KAF156 exposure is also increased when co-administered with LUM-SD formulation, by 2 to 3-fold (mean) (see FIGS. 3A and 3B, and table below).

| KAF156 | | Phase 2 (Combo) | | Phase 5 (Mono) | |
|---|---|---|---|---|---|
| | | Mean | SD | Mean | SD |
| T½ | (h) | 31.0 | 8.6 | 33.2 | 6.5 |
| Tmax | (h) | 3.3* | 4.0 | 1.0 | 0.0 |
| Cmax | (ng/mL) | 1204 | 465 | 451 | 213 |
| AUClast | (h*ng/mL) | 36710 | 7382 | 11632 | 5472 |
| AUCinf | (h*ng/mL) | 45360 | 5394 | 14435 | 6130 |

*$T_{max}$ were 1, 1, 8 hr in 3 dogs, respectively.

different combination regimens were simulated using the final models. Summary statistics for concentration on day 6 and day 7, proportion of patients who have concentration on day 7 above 200 ng/mL for LUM-SDF variant-1, proportion of patients who have concentrations on day 6 and on day 7 above 58 ng/mL for KAF156, $C_{max}$, $AUC_{inf}$ were calculated. Likelihood of success of a given LUM-SDF variant-1 dose level was calculated as the percentage of patients receiving this given dose who have lumefantrine day 7 plasma concentrations above 200 ng/mL; likelihood of success of a given KAF156 dose level was calculated as the percentage of patients receiving this given dose who have KAF156 day 6 plasma concentrations above 58 ng/mL. The likelihood of combination treatment success was calculated assuming independent effects of its components without any synergetic effect.

For the PK simulations of different combination regimens, inter-individual variability was taken into account; residual variability was not taken into account. Estimated

| | Ratio (Phase 2:Phase 5) | | | | |
|---|---|---|---|---|---|
| KAF156 | Dog 1 | Dog 2 | Dog 3* | Mean | SD |
| Cmax | 2.6 | 2.5 | 3.3 | 2.8 | 0.4 |
| AUClast | 2.7 | 2.9 | 5.2 | 3.6 | 1.4 |
| AUCinf | 2.6 | 2.8 | 5.3 | 3.6 | 1.5 |

| | $T_{1/2}$ (h) | $T_{max}$ (h) | $C_{max}$ (ng/mL) | $C_{max}$/D (ng/mL/mg) | $AUC_{last}$ (h*ng/mL) | $AUC_{INF}$ (h*ng/mL) | $AUC_{INF}$/D (h*ng/mL/mg) |
|---|---|---|---|---|---|---|---|
| Phase 2 (SD sachet co-dosed with KAF156) | 19.1 ± 7.4 | 4 ± 0 | 4110 ± 487 | 274 ± 32.5 | 36400 ± 6606 | 37317 ± 6425 | 2488 ± 428 |
| Phase 4 (SD sachet) | 23.8 ± 9.2 | 3.3 ± 1.2 | 1910 ± 401 | 127 ± 26.7 | 24380 ± 11968 | 25443 ± 11816 | 1696 ± 788 |

*dog 3 had emesis after dosing in Phase 5, i.e., possible dose lose

When KAF156 is co-administered with lumefantrine, both lumefantrine and KAF156 exposures significantly increased.

Example 7: Population Pharmacokinetics Model

One population PK model for KAF156 and one population PK model for LUM-SDF variant 1 were implemented in Monolix 4.4.0 as part of Monolix Suite 2016R1 (Lixoft, Paris, France) using the SAEM algorithm. Simulations were performed using simulx function of mlxR 3.1.0 package in R-3.2.3. The final models were used to perform simulations for different dosing regimens. Individual PK profiles for KAF156 and LUM-SDF variant-1 up to 500 hours under covariance matrices of the random effects ("Omega matrices") were used. Parameter uncertainty was not taken into account for the simulations, i.e. point estimates of model parameters were used. Body weight effect was taken into account for the simulations. Dose proportionality was assumed for these simulations. The likelihood of combination treatment success was calculated assuming independent effects of its components without any synergetic effect between KAF156 and lumefantrine as ptot=1−(1−p1)(1−p2), where p1 is the likelihood of success for KAF156 and p2 is the likelihood of success for lumefantrine.

Results: The simulation outcome for the exposure and probability of treatment success are presented in below Tables A and B, respectively.

TABLE A

Simulated exposure of KAF156 and lumefantrine and combination treatment:

| Dose/regimen | Lumefantrine day 7, concentrations, ng/mL | KAF156 day 6 concentrations, ng/mL | Likelihood of combination treatment success |
|---|---|---|---|
| KAF156 400 mg + LUM-SDF 960 mg QD for 1 day | 162 [73-387] | 32 [13-81] | 45% |
| KAF156 800 mg + LUM-SDF 960 mg QD for 1 day | 162 [73-387] | 63 [26-162] | 72% |
| KAF156 400 mg + LUM-SDF 960 mg QD for 2 days | 358 [160-859] | 80 [34-195] | 97% |
| KAF156 200 mg + LUM-SDF 480 mg QD for 3 days | 383 [173-888] | 75 [33-178] | 97% |

TABLE A-continued

Simulated exposure of KAF156 and lumefantrine and combination treatment:

| Dose/regimen | Lumefantrine day 7, concentrations, ng/mL | KAF156 day 6 concentrations, ng/mL | Likelihood of combination treatment success |
|---|---|---|---|
| KAF156 400 mg + LUM-SDF 480 mg QD for 3 days | 383 [173-888] | 150 [65-356] | 100% |
| KAF156 400 mg + LUM-SDF 960 mg QD for 3 days | 602 [267-1439] | 150 [65-356] | 100% |

TABLE B

The likelihood of treatment success:

| Dose/regimen | LUM-SDF alone | KAF156 alone | Likelihood of combination treatment success |
|---|---|---|---|
| KAF156 400 mg + LUM-SDF 960 mg QD for 1 day | 34% | 16% | 45% |
| KAF156 800 mg + LUM-SDF 960 mg QD for 1 day | 34% | 57% | 72% |
| KAF156 400 mg + LUM-SDF 960 mg QD for 2 days | 89% | 72% | 97% |
| KAF156 200 mg + LUM-SDF 480 mg QD for 3 days | 91% | 70% | 97% |
| KAF156 400 mg + LUM-SDF 480 mg QD for 3 days | 91% | 97% | 100% |
| KAF156 400 mg + LUM-SDF 960 mg QD for 3 days | 98% | 97% | 100% |

The simulations suggest that under fasting conditions, the 3-day doses and the 2-day doses of KAF156 and LUM-SDF combinations have a relatively high likelihood of success (at least 97%). High single dose regimen KAF156 800 mg+LUM-SDF 960 mg QD for 1 day has a lower likelihood of success (72%), as well as the low single dose regimen KAF156 400 mg+LUMSDF 960 mg QD for 1 day (45%).

Example 8: Open-Label, Randomized, Parallel-Group Study in Adults and Children with Confirmed and Uncomplicated *P. falciparum* Malaria This study is set up in a two-part sequential design.
Part A:
Approximately 325 male and female adult/adolescent patients (≥12 years old and ≥35.0 kg) will be enrolled in Part A of the study.

At screening, eligible patients will be randomized into one of the seven cohorts, i.e., six KAF156 and LUM-SDF (Solid Dispersion Formulation) dose combinations and a control arm, in 2:2:2:2:2:2:1 ratios:

Cohort 1: KAF156 400 mg and LUM-SDF 960 mg once daily (QD) for 1 day
Cohort 2: KAF156 800 mg and LUM-SDF 960 mg QD for 1 day
Cohort 3: KAF156 400 mg and LUM-SDF 960 mg QD for 2 days
Cohort 4: KAF156 200 mg and LUM-SDF 480 mg QD for 3 days
Cohort 5: KAF156 400 mg and LUM-SDF 480 mg QD for 3 days
Cohort 6: KAF156 400 mg and LUM-SDF 960 mg QD for 3 days
Cohort 7: Coartem® twice a day (BID) for 3 days (dosing as per product label).

The infection will be measured through PCR-corrected adequate clinical and parasitological response (ACPR). PCR-Uncorrected ACPR at Days 15, 29 and 43 (i.e. 14, 28 and 42 days postdose), and PCR-corrected ACPR at Days 15 and 43 (i.e. 14 and 42 days post-dose) will be performed. Incidence rate of recrudescence and reinfection at Days 15, 29 and 43 will be measured, as well as Parasite and Fever Clearance Times (PCT and FCT). Proportion of patients with parasitaemia at 12, 24, and 48 hours after treatment will be estimated.

Part B:
Approximately up to 175 children (2 to <12 years old and ≥10.0 kg) with uncomplicated *P. falciparum* malaria will be randomized to up to three KAF156 and LUM-SDF dose combinations and the control arm in 2:1 ratios (2 patients for each KAF156 and LUM-SDF dose combination and 1 patient for control).

Eligible patients will be enrolled into one out of the up to four dosing cohorts i.e. up to three investigational drug dosing arms and a control arm. Dosing will be adjusted based on children's body weight similar to the adjustment of Coartem®.

KAF156 and LUM-SDF: up to 3 cohorts selected depending on the outcome of Part A—Coartem® BID for 3 days Initially, 4-6 children in the age range of 6 to <12 years will be included in Part B to confirm that KAF156 and LUM-SDF PK/drug exposure is consistent with Part A and that the assumption in dosing is correct in these cohorts. Following confirmation of drug exposure in these children, the additional patients will be included in Part B of the study.

Study design, procedures and assessments are the same in Part A and Part
Inclusion Criteria
Patients eligible for inclusion in this study must fulfill all of the following criteria:
Demography:
Part A: male and female patients ≥12 years and with a body weight ≥35.0 kg
Part B: after determining the effective/tolerated doses and regimens in adolescent and adult patients, male and female patients ≥2 and <12 years and with a body weight ≥10.0 kg will be included
Health Status:
Microscopic confirmation of *P. falciparum* by Giemsa-stained thick and thin films
*P. falciparum* parasitaemia of more than 1000 and less than 150 000 parasites/µL at the time of screening
Axillary temperature ≥37.5° C. or oral/tympanic/rectal temperature ≥38.3° C.; or similar history of fever during the previous 24 hours (history of fever must be documented)
Negative pregnancy test for women of child bearing potential (WOCBP)

Exclusion Criteria

Patients fulfilling any of the following criteria are not eligible for inclusion in this study.

Medical history and clinical status:

1. Mixed *Plasmodium* infections
2. Signs and symptoms of severe malaria according to WHO 2015 criteria unless characterized by high parasitaemia only
3. Active infections including tuberculosis
4. Patients with concurrent febrile illnesses (e.g., typhoid fever)
5. History of, or current alcohol misuse/abuse defined as five or more drinks on the same occasion on each of 5 or more days in the past 30 days
6. Known relevant liver disease e.g. chronic hepatitis, cirrhosis, compensated or decompensated, history of hepatitis B or C, hepatitis B or A vaccination in last 3 months, known gallbladder or bile duct disease, acute or chronic pancreatitis
7. Any confirmed or suspected immunosuppressive or immunodeficient condition, including human immunodeficiency virus (HIV) infection
8. Severe malnutrition (body mass index (BMI)<16.0 for patients ≥12 years, and less than 70% of median normalized WHO reference weight for children <12 years)
9. Severe vomiting, defined as more than 3 times in the 24 hours prior to inclusion in the study or severe diarrhea defined as more than 3 watery stools per day
10. Pregnant or nursing (lactating) women
11. Sexually active patients not willing to practice effective contraception
12. Women of child bearing potential, defined as all women physiologically capable of becoming pregnant, unless they are using highly effective methods of contraception during dosing and for the duration of the study.
13. Active duodenal ulcer, ulcerative colitis, Crohn's disease, chronic (i.e. >2 weeks) use of non-steroidal anti-inflammatory drugs (NSAIDs)
14. Clinically relevant abnormalities of electrolyte balance which require correction, e.g. hypokalemia, hypocalcemia or hypomagnesemia.
15. Anemia (Hemoglobin level <8 g/dL)
16. Any surgical or medical condition which might significantly alter the absorption, distribution, metabolism, or excretion of drugs, or which may jeopardize the patient in case of participation in the study. The investigator should make this determination in consideration of the patient's medical history and/or clinical or laboratory evidence of any of the following:

AST/ALT >2× the upper limit of normal range (ULN), regardless of the level of total bilirubin AST/ALT >1.5 and ≤2×ULN and total bilirubin is >ULN Total bilirubin >2×ULN, regardless of the level of AST/ALT 17. Resting QTcF >450 ms (males), QTcF >460 ms (females) at screening
18. Creatinine >2×ULN in the absence of dehydration. In the case of dehydration, the creatinine should be <2×ULN after oral/parenteral rehydration
19. History of malignancy of any organ system (other than localized basal cell carcinoma of the skin or in situ cervical cancer), treated or untreated, within the past 5 years, regardless of whether there is evidence of local recurrence or metastases
20. Known chronic underlying disease such as sickle cell disease, and severe cardiac, renal, or hepatic impairment
21. Known active or uncontrolled thyroid disease
22. Inability to tolerate oral medication (in tablet and/or liquid form) Interfering substances
23. Patients with prior antimalarial therapy within 2 months of screening
24. Use of any antibiotics with antimalarial activity within 4 weeks of screening
25. Use of other investigational drugs within 5 half-lives of enrollment, or within 30 days or until the expected pharmacodynamic effect has returned to baseline, whichever is longer
26. Patients taking medications prohibited by the protocol
27. Previous participation in any malaria vaccine study or received malaria vaccine in any other circumstance.

The invention claimed is:

1. A pharmaceutical combination comprising about 400 mg to about 1000 mg lumefantrine formulated as a solid dispersion and about 200 mg to about 1000 mg of 2-amino-1-(2-(4-fluorophenyl)-3-(4-fluorophenylamino)-8,8-dimethyl-5,6-dihydroimidazo[1,2-a]pyrazin-7(8H)-yl)ethanone, or a pharmaceutically acceptable salt thereof.

2. The pharmaceutical combination according to claim 1, comprising about 200 mg, about 400 mg or about 800 mg of 2-amino-1-(2-(4-fluorophenyl)-3-(4-fluorophenylamino)-8,8-dimethyl-5,6-dihydroimidazo[1,2-a]pyrazin-7(8H)-yl) ethanone, or a pharmaceutically acceptable salt thereof.

3. The pharmaceutical combination according to claim 1, comprising about 400 mg to about 500 mg or about 900 mg to about 1000 mg of lumefantrine.

4. The pharmaceutical combination according to claim 1, comprising about 480 mg or about 960 mg of lumefantrine.

5. The pharmaceutical combination according to claim 1, comprising about 200 mg of 2-amino-1-(2-(4-fluorophenyl)-3-(4-fluorophenylamino)-8,8-dimethyl-5,6-dihydroimidazo[1,2-a]pyrazin-7(8H)-yl)ethanone and about 480 mg of lumefantrine.

6. The pharmaceutical combination according to claim 1, comprising about 400 mg of 2-amino-1-(2-(4-fluorophenyl)-3-(4-fluorophenylamino)-8,8-dimethyl-5,6-dihydroimidazo[1,2-a]pyrazin-7(8H)-yl)ethanone and about 480 mg of lumefantrine.

7. The pharmaceutical combination according to claim 1, comprising about 400 mg of 2-amino-1-(2-(4-fluorophenyl)-3-(4-fluorophenylamino)-8,8-dimethyl-5,6-dihydroimidazo[1,2-a]pyrazin-7(8H)-yl)ethanone and about 960 mg of lumefantrine.

8. The pharmaceutical combination according to claim 1, comprising about 800 mg of 2-amino-1-(2-(4-fluorophenyl)-3-(4-fluorophenylamino)-8,8-dimethyl-5,6-dihydroimidazo[1,2-a]pyrazin-7(8H)-yl)ethanone and about 960 mg of lumefantrine.

9. The pharmaceutical combination according to claim 1, which is a fixed dose combination.

10. The pharmaceutical combination according to claim 1, which is a non-fixed dose combination.

11. A method of preventing or treating malaria, or delaying the symptoms or ameliorating the conditions associated with malaria, in a subject in need thereof, comprising administering to said subject compound 2-amino-1-(2-(4-fluorophenyl)-3-(4-fluorophenylamino)-8,8-dimethyl-5,6-dihydroimidazo[1,2-a]pyrazin-7(8H)-yl)ethanone, or a pharmaceutically acceptable salt thereof, administrated daily at a dose of about 200 mg to about 1000 mg, with lumefantrine formulated as a solid dispersion, wherein the lumefantrine is administered daily at a dose of about 400 mg to about 1000 mg.

12. The method according to claim 11, wherein said compound is administered at a dose of about 200 mg, about 400 mg or about 800 mg.

13. The method according to claim 11, wherein said compound is administered daily during 1 to 3 days.

14. The method according to claim 11, wherein the lumefantrine is administered daily at a dose of about 400 mg to about 500 mg or about 900 mg to 1000 mg.

15. The method according to claim 11, wherein, the lumefantrine is administrated daily at a dose of 480 mg or 960 mg.

16. The method according to claim 11, wherein the compound is administered daily at a dose of about 200 mg and the lumefantrine is administered daily at a dose of about 480 mg.

17. The method according to claim 11, wherein the compound is administered daily at a dose of about 400 mg and the lumefantrine is administered daily at a dose of about 480 mg.

18. The method according to claim 11, wherein the compound is administered daily at a dose of about 400 mg and the lumefantrine is administered daily at a dose of about 960 mg.

19. The method according to claim 11, wherein the compound is administered daily at a dose of about 800 mg and the lumefantrine is administered daily at a dose of about 960 mg.

20. The method according to claim 11, wherein the compound and the lumefantrine is used in a non-fixed dose combination.

21. The method according to claim 11, wherein the compound and the lumefantrine is used in a fixed dose combination.

* * * * *

UNITED STATES PATENT AND TRADEMARK OFFICE
CERTIFICATE OF CORRECTION

| | | |
|---|---|---|
| PATENT NO. | : 11,738,028 B2 | Page 1 of 1 |
| APPLICATION NO. | : 17/388277 | |
| DATED | : August 29, 2023 | |
| INVENTOR(S) | : Jain et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 53 days.

Signed and Sealed this
First Day of July, 2025

Coke Morgan Stewart
*Acting Director of the United States Patent and Trademark Office*